United States Patent [19]

McCall

[11] 3,996,162
[45] Dec. 7, 1976

[54] ANALYTICAL SORBENT AND METHOD OF USE

[75] Inventor: Mary S. McCall, Dallas, Tex.

[73] Assignee: Nuclear Medical Laboratories, Inc., Dallas, Tex.

[22] Filed: Mar. 1, 1974

[21] Appl. No.: 447,217

Related U.S. Application Data

[63] Continuation of Ser. No. 15,216, Feb. 27, 1970, abandoned.

[52] U.S. Cl. .............................. 252/430; 252/428; 252/437; 252/440; 252/443; 252/454; 252/455 R; 252/457; 252/459; 252/463; 424/1; 252/408; 23/230 B; 23/252 R
[51] Int. Cl.$^2$ ........................................ G01N 33/16
[58] Field of Search .......... 252/437, 440, 443, 454, 252/455 R, 457, 459, 463, 428, 430, 472, 475, 476

[56] References Cited

UNITED STATES PATENTS

| | | | |
|---|---|---|---|
| 2,413,184 | 12/1946 | La Lande | 252/463 X |
| 2,451,564 | 10/1948 | La Lande | 252/457 X |
| 2,549,921 | 4/1951 | Mosley | 252/440 X |
| 2,699,430 | 1/1955 | Teter | 252/457 X |
| 2,760,939 | 8/1956 | Den Herder | 252/457 |

Primary Examiner—Patrick P. Garvin
Attorney, Agent, or Firm—Richards, Harris and Medlock

[57] ABSTRACT

An analytic sorbent material is prepared by wetting a particulate inorganic crystalline lattice material, such as magnesium silicate with an aqueous fluid such as a barbital buffer solution or distilled water, and thereafter heating the wetted sorbent until its sorption capacity stabilizes.

13 Claims, No Drawings

ANALYTICAL SORBENT AND METHOD OF USE

This application is a continuation of co-pending application Ser. No. 15,216, now abondoned, filed Feb. 27, 1970.

This invention relates to analytical sorbent material. In another aspect, this invention relates to diagnostic tests for the determination of the level of thyroid hormone within a body fluid.

Various sorbent materials are used in the art for the separation of protein type constituents such as amino acids, proteins, polypeptides, and hormones, and metals such as iron from fluids in various assays.

For example, various diagnostic tests are known in the art for determining thyroid function. Among the most accuracte tests available are the diagnostic tests which utilize radioisotope labeled hormones to indirectly determine the level of thyroid hormones, thyroxine ($C_{15}H_{11}I_4NO_4$), and triiodothyronine ($C_{15}H_{12}I_3NO_4$) present in body fluids.

Specifically, these tests include a test commonly referred to as the T-3 test, which measures the unsaturated binding capacity of thyrobinding globulin and other proteins within a body fluid such as blood, and the test commonly referred to as the T-4 test which measures the total quantity of hormone within a sample of blood serum.

Both of these tests include the steps of adding the radiosotope labeled hormone to a solution containing a sample of hormone produced within the body and thyrobinding globuin, separating the resulting thyrobinding globulin containing bound hormone from the resulting unbound hormone, and counting the radioactivity of either the bound or unbound hormone. This counting procedure will indirectly indicate the amount of endogenous hormone which is bound to the natural globulin and protein binding sites within the blood.

Thus, both the T-3 and the T-4 tests depend for their accuracy upon the efficient separation between the bound and unbound thyroid hormone in the test sample. The currently available methods for removal of these hormones include ion exchange resins such as the ion exchanger having strongly basic amino or quatenary ammonium groups as described in U.S. Pat. No. 3,414,383. These organic ion exchange resins can be either in loose forms, or incorporated in polyurethane structures as disclosed in U.S. Pat. No. 3,206,602, or enclosed in porous bags or the like. Another available method involves a selective adsorption of the free hormones by charcoal which has been coated with suitable proteins.

The major disadvantages of the separation methods described above, is that the binding of the hormones to the separation material is both time and temperature dependent, so that the binding of the hormones to these materials increases with time and increasing temperatures. For example, as time increases, much of the protein bound thyroid hormone is ultimately bound to the ion exchange resin. In addition, from 1 to 2 hours are required for complete binding to take place with the ion exchange resins, further limiting the number of measurements which are possible in the laboratory. Also, coated charcoal must be enclosed within a heat block under controlled time and temperature conditions during the separation procedure. Thus, careful timing and controlled temperatures are necessary in the above-described conventional T-3 and T-4 tests when separating the thyroid hormones bound to the natural binding sites within the blood (thyrobinding globulin and other proteins) from the nonbound thyroid hormones.

Recently, an improved thyroid hormone test has been developed and is set forth in copending application Ser. No. 846,289, now U.S. Pat. No. 3,666,854. This new test includes sorbing the free hormones on a particulate, inorganic crystalline lattice material, such as magnesium silicate, for example. This new test is neither time nor temperature dependent, in that it can be carried out at any convenient room temperature over any convenient time period to obtain very accurate results. The sorbent will quickly and efficiently bind only the free or nonprotein bound thyroid hormone within a sample fluid. This test normally includes the admixing of the dry sorbent material with a suitable solution, such as a barbital buffer solution containing both the free hormones and the hormones bound to the natural binding sites (thyrobinding globulin and other proteins), thoroughly admixing until sorption of the free hormones and then separation of the sorbent from the resultant supernatant fluid.

One object of this invention is to provide an improved sorbent, and method of preparing same which can be used in diagnostic tests, such as for removing free thyroid hormones from a sample solution in a thyroid diagnostic test.

Another object of this invention is to provide an improved thyroid hormone test.

A further object of this invention is to provide an improved thyroid hormone test procedure which utilizes a particulate inorganic crystalline lattice material to separate free hormones from bound hormones in a sample.

According to one embodiment of this invention, it has been found that when a particulate crystalline lattice material is wetted by an aqueous fluid, and heated, its sorption capacity for protein-type material will stabilize. It is noted that the sorption capacity of the particulate inorganic crystalline lattice materials for protein-type materials such as thyroid hormones, in aqueous solution does not fluctuate with time and with normal variations of room temperature, e.g., variations of from 10° to 20° C, in the test procedures as described in said copending application Ser. No. 846,289, now U.S. Pat. No. 3,666,854. However, it has been found that when the particulate inorganic crystalline material is added to an aqueous solution as a premixture and subjected to extreme temperature conditions, its sorption capacity will vary (generally decrease) until a stable plateau is reached. Thus, according to one embodiment of this invention, it has been found that particulate crystalline inorganic lattice material can be preweighed and wetted in a suitable aqueous medium, such as a barbital buffer in a packaged unit and then heated until the sorption capacity thereof shows no substantial variance. The resulting dispersion is now suitable for storage and shipment as an integral portion of a test kit, for example, a test kit for thyroid hormones which can also contain in the kit a radioactive isotope labeled hormone solution, and if desired, a standard solution of thyrobinding globulin. The resulting test kit containing this dispersion can be shipped and stored even under extremely warm conditions, i.e., above 140° F and still yield very accurate reproducible results when finally utilized.

According to another embodiment of this invention, an improved test procedure for thyroid hormones is provided using the stable dispersion of particulate inorganic crystalline lattice material of the first embodiment.

Thus, the sorbent dispersions which are prepared in accordance with this invention can be stored lengthy time periods under extreme ranges of temperature without affecting the sorbent capacity of the inorganic crystalline lattice material.

The particulate inorganic crystalline material which can be used within the scope of this invention includes the phosphates, oxides, hydroxides, silicates, aluminates, and sulfates, of the metallic elements in Groups IA, IIA, IIIA, IIB and VIII of the Periodic Table as illustrated on page B-2 of the *Handbook of Chemistry and Physics*, Chemical Rubber Publishing Company (1964).

Examples of suitable materials include calcium carbonate, calcium phosphate, calcium oxide, calcium hydroxide, calcium silicate, calcium aluminate, calcium sulfate, magnesium carbonate, magnesium phosphate, magnesium oxide, magnesium hydroxide, magnesium silicate, magnesium aluminate, magnesium sulfate, aluminum carbonate, aluminum phosphate, aluminum oxide, aluminum hydroxide, aluminum silicate, aluminum sulfate, potassium carbonate, potassium phosphate, potassium oxide, potassium hydroxide, potassium silicate, potassium aluminate, potassium sulfate, iron carbonate, iron phosphate, iron oxide, iron hydroxide, iron silicate, iron aluminate, iron sulfate, barium carbonate, barium phosphate, barium oxide, barium hydroxide, barium silicate, barium aluminate, barium sulfate, zinc carbonate, zinc phosphate, zinc oxide, zinc hydroxide, zinc silicate, zinc aluminate, zinc sulfate, and mixed salts thereof, and silicic acid.

Some specific examples of commonly occuring materials which can be used within the scope of this invention include: Opal, $(Si(OH)_4+SiO_2$; Waterglass, $Si_4O_9.Na_2$; Kaolinite, $Al_2(SiO_5)(OH)_4$; Dickite, $Al_2(Si_2O_5)(OH)_4$; Nacrite, $Al_2(Si_2O_5)(OH)_4$; Metahalloysite, $Al_2.(Si_2O_5)(OH)_4$; Halloysite $Al_2(SiO_3)(OH)_3$; Attapulgite, $Mg_3(Si_4O_{10})(OH)_2(OH).2H_2O$, $Al(Si_4O_{10})(OH)_2$; Pyrophyllite, $Al_2(Si_4O_{10})(OH)_2$; Talc, $Mg_3(Si_4O_{10})(OH)_2$; Montmorillonite, $Al_2(Si_4O_{10})(OH)_2.xH_2O$, $Mg(Si_4O_{10})(OH_2.xH_2O)$; Montronite, $Fe_2(Si_4O_{10})(OH)_2.xH_2O$, $Mg(Si_4O_{10})(OH)_2.xH_2O$; Beidellite, $Al_2.(Si_4AlO_{10})(OH)_2.xH_2O$, $Mg(Si_4AlO_{10})(OH)_2.x\ H_2O$; Saponite, $Mg_3(Si_4O_{10})(OH)_2.xH_2O$, Illite, $K_y.Al_2(Si_{4-y})O_{10}$, $Fe_2.Mg_2.Mg_3(Si_{4-y}.Al_y)O_{10}$; Muscovite, $K.Al_2(AlSi_3O_{10})(OH)_2$; Paragonite, $Na.Al_2(AlSi_3O_{10})(OH)_2$; Phlogonite, $K.Mg_3(AlSi_3O_{10})(OH)_2$; Biotite, $K.(Mg_1Fe)_3(AlSi_3O_{10})(OH)_2$; Margarite, $Ca.Al_2(Al_2.Si_3O_{10})(OH)_2$.

The most preferred inorganic crystalline sorbent materials include the silicates, particularly magnesium silicate and aluminum silicate.

The inorganic crystalline sorbent material is preferably in colloidal form (an average diameter of from $10^{-7}$ to $10^{-4}$ centimeters). However, the sorbent material can have a non-colloidal particle size of from 4 mesh to 325 mesh. (U.S. Standard). When using non-colloidal particles, it is preferred that particle size range from 100 mesh to 325 mesh (U.S. Standard).

The particular aqueous carrier medium can vary with the individual test. For example, when the sorbent is to be used in a thyroid hormone test such as a determination of unsaturated binding capacity of thyrobinding globulin and other proteins, or a test for total serum thyroxine the aqueous carrier fluid can be a barbital buffer solution (diethyl barbituric acid pH 8.6, 0.075 M). Other suitable aqueous buffer solutions incude solutions with a pH ranging from 6.8 to 9.6 containing buffers such as tris (hydroxymethyl) aminomethane, tris (hydroxymethyl) aminomethane maleate, sodium phosphate, and potassium phosphate. Aqueous carriers other than buffer solutions include standard aqueous saline solution, or distilled water.

In each particular test the amount of the particulate inorganic crystalline lattice material and the aqueous carrier can be varied according to the situation. Specifically, the amount of sorbent material which is utilized can be varied as desired to yield the optimum spread between normalcy and abnormalcy. For example, it has been found that when utilizing colloidal size magnesium silicate as the sorbent in a thyroid hormone test, in order to get a normal range of from 35 to 45% binding of free thyroid hormone, about 60 grams per liter of the magnesium silicate should be present in the aqueous medium which is treated in accordance with this invention. The amount of sorbent can be varied as desired by correlating the concentration of the particulate inorganic crystalline lattice material in the test solution versus the percent binding capacity of the material. The desired workable range can then be determined by one skilled in the art.

Various pre-treatment times and temperatures can be used in the scope of this invention to yield quite stable sorbent material. It is only necessary that the aqueous suspension of sorbent materials be treated for a time sufficient to yield a relatively stable sorbent capacity. Once the suspension of particulate inorganic crystalline material has been formed, any temperature from room temperature to the boiling temperature of the aqueous carrier can be utilized to stabilize the material. It is generally preferred that the treatment temperature be at an elevated temperature above room temperature (above about 25° C) to the boiling point of the aqueous fluid, and more preferably at a temperature above 60° C. The treatment causes the binding capacity of the sorbent to vary (generally decrease) until it reaches a relatively stable plateau wherein further heat treatment will not cause a substantial variation in the binding capacity. For uses in thyroid hormone tests, it is preferred that the treatment occur until percent binding or uptake will not vary greater than about plus or minus 1.5% and more preferably about a plus or minus 1%. This means that the binding capacity of the treated sorbent material will not vary more than 1.5% when subjected to subsequent elevated temperatures. The percent binding or percent uptake is defined as the percentage of free radioisotope labeled hormone bound by the sorbent from a test sample based upon total amount of free radioisotope labeled hormone which was added to the test sample.

For most particulate inorganic crystalline lattice material which can be used in this invention, suitable pre-treatment schedules include heating from 60° to 80° C for a time of from about 15 hours to 24 hours or more, heating at 40° C for a time of from 3 to 5 days or more, or heating at the boiling temperature of the aqueous fluid for a time in the range of from 1 to 2 hours. Once the binding capacity of the sorbent material has become stabilized to a degree desired, it can then be subsequently subjected to elevated temperatures over extended periods of time without deleteriously affecting the sorbent capacity thereof.

While it is herein understood that the scope of this invention is not limited to theory, it is believed that the sorption capacity of the particulate inorganic crystalline lattice material stabilizes in the presence of water and elevated temperature because of a recrystallization process. In essence, it is believed that the particulate material contains a substantial portion of broken crystal lattices which result in many high energy oxygen-rich and electron-rich sites existing at the edges of the crystal molecules. Thus, the resulting particulate structures tend to recrystallize and form a lower energy system in contact with water.

It is noted that the more hydrated a particulate inorganic crystalline lattice material is before dispersion in the aqueous fluid, the less change in the sorption capacity will occur during stabilization. However, some stabilization will always occur.

As set forth above, the stabilized aqueous dispersion of this invention is particularly useful in separating unbound thyroid hormones from hormones bound to natural binding sites (thyrobinding globulin and other proteins) in a diagnostic test. However, the stabilized dispersion of this invention can be utilized in other assays, such as amino acids, protein, peptide and polypeptide assays, and metal assays such as iron and the like.

When conducting tests for thyroid hormone, whether it be a test on unsaturated binding capacity of thyrobinding globulin and other proteins, or a test for total serum thyroxine, the general test procedures as set forth in copending application Ser. No. 846,289, now U.S. Pat. No. 3,666,843 can be utilized with the exception that the stable dispersion of this invention is used in each test.

When utilizing the stable dispersion of this invention (a suitable stabilized sorbent material, such as magnesium silicate, has been disposed in an appropriate amount of an aqueous carrier, such as a barbital buffer solution contained within a suitable receptacle, such as a test tube) in accordance with the preferred test procedure of this invention, the tube is first centrifuged to thoroughly pack the sorbent particles in the bottom thereof. Next, the serum to be tested is added to the tube and mixed with the supernatant fraction. After this, the radioactive tracer material, e.g., thyroid hormone labeled with $I^{125}$ or $I^{131}$, is mixed with the supernatant fluid. At any time thereafter, the tube is vigorously shaken, such as with a Vortex mixer for an appropriate period of time, for example, from 20 to 30 seconds, to substantially suspend and disperse the sorbent particles. Next, the tube is centrifuged to separate the sorbent material from the supernatant fluid. At this time either the supernatant fluid or the sorbent material, preferably the sorbent material, is counted with a scintillation well counter to determine the labeled hormone bound to or free from the thyrobinding globulin in the sample serum.

The percent free radioactive labeled hormone (percent uptake) is determined by determining the ratio of the sample counts per minute from the sorbent material to the total counts per minute of a standard amount of radioactive hormone which is equivalent to the total radioactive hormone initially added to the sample. This is accomplished by preparing a standard sample of the radioactive hormone either diluted with water to the same approximate volume as the packaged sorbent occupies in the bottom of the test tube, or adding the sample hormone to a duplicate quantity of sorbent in a test tube and then counting the resulting material to establish the standard counts per minute. In this manner, the counting efficiency of the standard will be identical to the counting efficiency of the unknown.

For most operations, the aqueous solution for each sample can be in the range of from 1 to 3 milliliters while the sorbent material used can be in the range of from 20 to 600 milligrams or more. A suitable quantity of serum sample includes 0.1 milliliter, and a tracer quantity of radioactive isotopes labeled triiodothyronine or thyroxine can be used. These values can vary with the particular sorbent utilized.

The following examples are given to better facilitate the understanding of this invention, and are not intended to limit the scope thereof.

EXAMPLE 1

This example is presented to illustrate the stabilizing effect of the heat treatment of the aqueous dispersion of the particulate inorganic crystalline lattice material as used in the scope of this invention. In all of the runs, a standard serum was utilized containing a known amount of thyroxine and thyroxine binding globulin. In addition, the term "percent uptake" used throughout these examples has been previously defined above and means the total counts per minute of the sample found in the adsorbent as a percentage of the total counts per minute of a standard amount of radioactive hormone which is equivalent to the total radioactive hormone initially added to each sample. Several samples were prepared by dispersing colloidal magnesium silicate in two milliliters of barbital buffer solutions (aqueous solutions of diethylbarbituric acid pH 8.6, 0.075M) in a quantity which equals 36 grams per liter. After each sample mixture was treated for a time and at a temperature indicated in Table I below it was then equilibrated to room temperature. Next, 0.1 milliliters of the standard serum and a tracer quantity of radioactive $I^{125}$ triiodothyronine was added thereto. Each sample was then thoroughly agitated for approximately 20 seconds in a Vortex mixer and then allowed to set for at least 4 minutes and then centrifuged. The resulting precipitate was counted in a scintillation well counter and compared to the total counts of the tracer quantity of radioactive isotope as described above to obtain the percent uptake. The percent uptake for the various samples are entered in Table I below:

TABLE I

| Treatment Hours | Time Days | Percent Uptake | | | | |
|---|---|---|---|---|---|---|
| | | −20° C | 5° C | 24° C | 50° C | 60° C |
| 0 | | 33% | 33% | 33% | 33% | 33% |
| 1 | | | | | | |
| 2 | | | | | 32.2% | 32.5% |
| 3 | | | | | | |
| 4 | | | | | | 31.7% |
| 6 | | | 33.9% | | 30.2% | 29.5% |
| 8 | | 32.5% | | | | 29.3% |
| 15–20 | | | 32.7% | | 27.3% | 25.3% |
| | 1 | | 32.0% | 32.1% | 27.8% | 25.4% |
| | 2 | | | 31.8% | 26.8% | 25.9% |
| | 3 | | 33.3% | 30.5% | 26.1% | |
| | 4 | | 31.3% | | | |
| | 5 | 31.9% | | | | |
| | 6 | | 32.2% | 30.8% | | |

As shown from Table I, the examples show no deviation with temperature when they are counted initially after the mixing procedure. However, as time progresses, the percent uptake varies for each sample. The samples treated for 2 days at 50° C and from 15 to 20 hours at 60° C stabilized and show a variance of no greater than plus or minus 1.5% uptake.

EXAMPLE 2

The mixing procedure of Example 1 was repeated except utilizing quantities of 60 grams per liter of the magnesium silicate in the aqueous barbital buffer solutions. These samples were then tested according to the same procedure as set forth in Example 1 to yield the results in Table II below:

TABLE II

| Time Min. | Exposed Hrs. | Exposed Days | Percent Uptake 40° | Temperature 80° | Temperature 97° |
|---|---|---|---|---|---|
| 0 |   |   | 49.3% | 49.3% | 52.3% |
| 10 |   |   |   |   | 45.9% |
| 30 |   |   |   |   | 42.9% |
|   | 1 |   |   |   | 40.9% |
|   | 2 |   |   |   | 41.3% |
|   | 3 |   |   |   | 40.7% |
|   |   | 1 | 46.6% | 42.9% |   |
|   |   | 2 | 44.7% | 42.5% |   |
|   |   | 3 | 42.3% |   |   |
|   |   | 4 | 42.4% |   |   |
|   |   | 5 | 42.1% |   |   |

The samples treated at 40° C showed a stabilization after 3 days of heat treatment whereas, the samples treated at 80° C were stabilized after 1 day of heat treatment and the samples treated at 97° C stabilized after 1–2 hours of heat treatment.

EXAMPLE 3

The procedure outlined in Example 1 above was performed with various times and temperatures on samples of barbital buffer containing 60 grams per liter of magnesium silicate to form several pretreated mixtures. Four sample mixtures (Classified as Mixtures A) were heated at 40° C for 5 days. Four sample mixtures (Classified as Mixtures B) were pretreated at 60° C for 1 day. Four sample mixtures (Classified as Mixtures C) were pretreated at 80° C for 1 day. Four sample mixtures (Classified as Mixtures D) were boiled (97° C) for 1 hour and 20 minutes. After the pretreatment procedures, one sample mixture each of A, B, C and D mixtures was then allowed to cool and then reheated to 60° C for 1, 2, and 3 days, respectively, and then tested for percent uptake according to the procedure outlined in Example 1. The results of the tests are set forth in Table III below:

TABLE III

| Reheat Time Held at 60° C (Days) | Percent Binding Sample Mixtures A | B | C | D |
|---|---|---|---|---|
| 0 | 42.1% | 40.1% | 43.3% | 42.7% |
| 1 | 40.8% | 39.8% | 41.1% | 43.1% |
| 2 | 41.7% | 41.4% | 42.7% | 44.2% |
| 3 | 42.3% | 42.2% | 42.5% | 44.1% |

As shown in Table III, the initial treating operations stabilized the sample mixtures such that subsequent heating operations to 60° C does not materially affect their binding capacity. This, therefore shows that the initial heat-treating operation serves to stabilize the solvent material wetted by the aqueous carrier. Thus, when sample mixtures are made up and subjected to the temperature extreme of 60° C (140° F) during storage or shipment, they can later be used very predictable and reproduceable results.

EXAMPLE 4

Several sample solutions were made up using different sorbents in the 2 milliliter aqueous barbital solutions described in Example 1.

Initially, 3 separate mixtures were made up. The sample mixtures (Mixture X) were each formed by adding kaolin (40% alumina and 55% silica) to 2 milliliters of barbital in an amount corresponding to 100 grams per liter. The sample mixtures (Mixture Y) were each made by adding calcium carbonate to a 2 milliliter barbital solution in an amount corresponding to 200 grams per liter. Sample mixtures (Mixture Z) were each made up by adding calcium phosphate (hydrated) to 2 milliliters of the barbital solution in an amount corresponding to 100 grams per liter. One sample each X, Y and Z were not preheated but were tested for percent uptake in accordance with the procedures set forth in Example 1. The results of the tests are indicated in the Table IV below. Next, 3 samples each of Mixtures X, Y and Z were subjected to heating for 1, 2, and 3 days respectively, at 60° C. After each pretreatment time and period, the percent uptake was tested in the manner described in Example 1 and is shown in Table IV below:

TABLE IV

| | Percent Uptake X | Y | Z |
|---|---|---|---|
| Before Treatment | 30.4% | 31.4% | 30.9% |
| After cooling and reheating (60°) for following times (Days) | | | |
| 1 | 25.6% | 11.7% | 29.2% |
| 2 | 26.9% | 12.7% | 29.0% |
| 3 | 28.1% | 12.7% | |

As shown in Table IV, the heat treatment stabilized the sorption capacity of each of the particulate inorganic sorbent materials.

The above examples clearly set forth the embodiment of this invention of forming a stabilized sorbent material in an aqueous carrier by heating the sorbent in the aqueous carrier until the sorption capacity thereof is stabilized, this heating operation generally results in a decrease of the sorption capacity until a plateau is reached wherein substantial deviation does not occur.

While this invention has been described in relation to its preferred embodiments, it is to be understood that the various modifications will now be apparent to one skilled in the art upon reading the specification, and it is intended to cover such modifications as fall within the scope of the appended claims.

I claim:

1. A method of preparing an analytical sorbent for an in vitro diagnostic test which has a stabilized sorbent capacity for endogenous material found in a body fluid selected from the group consisting of protein-type constituents and metals comprising:
   a. wetting a particular inorganic crystalline lattice material with an aqueous buffer solution, said particulate inorganic crystalline lattice material being selected from the group consisting of carbonates, phosphates, oxides, hydroxides, silicates, aluminates, and sulfates of the metallic elements in Groups IA, IIA, IIIA, IIB and VIII of the Periodic Table and mixed salts thereof; and b. heating the resulting dispersion at a temperature of from about 25° C to the boiling point of said aqueous buffer solution for a sufficient time to cause the sorbent capacity of said material to stabilize.

2. The method of claim 1 wherein said aqueous buffer solution contains buffers selected from the group consisting of barbital buffer, tris (hydroxymethyl) amino methane buffer, tris (hydroxymethyl) aminomethane maleate buffer, sodium phosphate buffer, and potassium phosphate buffer.

3. The analytical sorbent produced by the method of claim 2.

4. A method of preparing an analytical sorbent for an in vitro diagnostic test which has a stabilized sorbent capacity for endogenous material found in a body fluid selected from the group consisting of protein-type constituents and metals comprising:

a. wetting a particulate inorganic crystalline lattice material with a standard aqueous saline solution, said particulate inorganic crystalline lattice material being selected from the group consisting of carbonates, phosphates, oxides, hydroxides, silicates, aluminates, and sulfates of the metallic elements in Groups IA, IIA, IIIA, IIB and VIII of the Periodic Table and mixed salts thereof; and b. heating the resulting dispersion at a temperature of from about 25° C to the boiling point of said standard aqueous saline solution for a sufficient time to cause the sorbent capacity of said material to stabilize.

5. The analytical sorbent produced by the method of claim 4.

6. A method for preparing an analytical mixture containing a sorbent, for use in vitro diagnostic test which has a stabilized sorbent capacity for endogenous material found in a body fluid selected from the group consisting of protein-type constituents and metals, said mixture including an aqueous medium consisting essentially of an aqueous buffer solution and a particulate inorganic cyrstalline sorbent material selected from the group consisting of carbonates, phosphates, oxides, hydroxides, silicates, aluminates and sulfates of the metallic elements in Groups IA, IIA, IIIA, IIB and VIII of the Periodic Table and mixed salts thereof comprising:

a. admixing said aqueous buffer solution and said sorbent and thereafter heating the mixture at a temperature in the range of from about 25° C to the boiling point of said aqueous buffer solution until the percent uptake of said analytical sorbent for said endogenous material will not vary greater than about ±1.5 percent; and b. packaging the mixture of aqueous buffer solution and said stabilized sorbent material in a sealed container.

7. The packaged mixture produced by the method of claim 6.

8. The method of claim 6 wherein said aqueous medium is water which contains a buffer material selected from group consisting of diethyl barbituic acid, tris (hydroxymethyl) amine methane, tris (hydroxymethyl) amino methane maleate, sodium phosphate, and potassium phosphate.

9. The packaged mixture produced by the method of claim 8.

10. A packaged analytical mixture within a sealed container comprising a sorbent for use in an in vitro diagnostic test which has a stabilized sorbent capacity for endogenous material found in a body fluid selected from the group consisting of protein type constituents and metals, said mixture including an aqueous buffer solution containing a particulate inorganic crystalline sorbent material selected from the group consisting of carbonates, phosphates, oxides, hudroxides, silicates, aluminates and sulfates of the metallic elements in Groups IA, IIA, IIIA, IIB and VIII of the Periodic Table and mixed salts thereof, said sorbent having been stabilized by a process comprising mixing said sorbent with an aqueous fluid consisting essentially of water and thereafter heating the resulting mixture at a temperature in the range of from about 25° C to the boiling point of said water for a sufficient time to cause the sorbent capacity of said material for said endogenous material to stabilize.

11. The product of claim 10 wherein said aqueous buffer solution contains a buffer material selected from the group consisting of barbital buffer, tris(hydroxymethyl) amino methane buffer, tris(hydroxymethyl) amino methane maleate buffer, sodium phosphate buffer and potassium phosphate buffer.

12. A material for receiving and sorbing protein-type material in a clinical test procedure comprising an aqueous barbital buffer solution having dispersed therein a particulate inorganic crystalline lattice material selected from the group consisting of carbonates, phosphates, oxides, hydroxides, silicates, aluminates, and sulfates of the metallic elements in Groups IA, IIA, IIIA, IIB and VIII of the Periodic Table, and mixed salts thereof, which has been heated to a temperature of from about 25° C to the boiling point of said solution for a sufficient time to cause the sorbent capacity of said material to stabilize for said protein-type material.

13. A method of treating a particulate inorganic crystalline lattice material selected from the group consisting of carbonates, phosphates, oxides, hydroxides, silicates, aluminates and sulfates of the metallic elements in Groups IA, IIA, IIIA, IIB and VIII of the Periodic Table, and mixed salts thereof, comprising wetting said material with an aqueous barbital buffer solution and thereafter heating the wetted material at a temperature of from about 25° C to the boiling point of said barbital buffer solution for a sufficient time to cause the sorbent capacity of said material to stabilize.

* * * * *

PO-1050
(5/69)

UNITED STATES PATENT OFFICE
CERTIFICATE OF CORRECTION

Patent No. 3,996,162      Dated December 7, 1976

Inventor(s) Mary S. McCall

It is certified that error appears in the above-identified patent and that said Letters Patent are hereby corrected as shown below:

Col. 1, line 4, "abondoned" should be --abandoned--.
Col. 5, line 32, "3,666,843" should be --3,666,854--;
       line 37, "disposed" should be --dispersed--.
Col. 8, line 3, "be used very" should be --be used and give very--;
       line 65, "particular" should be --particulate--.
Col. 10, line 19, "hudroxides" should be --hydroxides--.

Signed and Sealed this

First Day of March 1977

[SEAL]

Attest:

RUTH C. MASON
Attesting Officer

C. MARSHALL DANN
Commissioner of Patents and Trademarks